United States Patent [19]

Saringer

[11] Patent Number: 4,537,083
[45] Date of Patent: Aug. 27, 1985

[54] DEVICE FOR IMPARTING CONTINUOUS PASSIVE MOTION TO HUMAN JOINTS

[75] Inventor: John H. Saringer, Toronto, Canada

[73] Assignee: Imasco-CDC Research Foundation, Toronto, Canada

[21] Appl. No.: 660,704

[22] Filed: Oct. 15, 1984

Related U.S. Application Data

[62] Division of Ser. No. 362,896, Mar. 29, 1982, Pat. No. 4,487,199.

[30] Foreign Application Priority Data

Oct. 23, 1981 [CA] Canada ................................ 388659

[51] Int. Cl.³ ............................................ F16H 27/02
[52] U.S. Cl. ..................... 74/89.15; 128/52; 74/424.8 R
[58] Field of Search ..................... 128/25 R, 26, 52; 74/89.15, 424.8 R

[56] References Cited

U.S. PATENT DOCUMENTS

| 3,220,718 | 11/1965 | Wikkerink | 74/89.15 |
| 3,546,930 | 12/1970 | Flarsheim | 74/89.15 |
| 4,077,268 | 3/1978 | Hill | 74/89.15 |

Primary Examiner—Richard J. Apley
Assistant Examiner—David J. Brown
Attorney, Agent, or Firm—Bachman and LaPointe

[57] ABSTRACT

A portable apparatus for imparting continuous passive motion to a human joint. A support is provided for harnessing to parts of the body at one side of the joint and conveyor means movable relative to the support is provided for connection to a part at the other side of the joint, so that the latter forms a link which is flexed as the conveyor means moves back and forth relative to the support. Drive means insures that a substantially continuous slow rhythmic reciprocating movement is applied to the joint.

12 Claims, 8 Drawing Figures

DEVICE FOR IMPARTING CONTINUOUS PASSIVE MOTION TO HUMAN JOINTS

This is a division of application Ser. No. 362,896 filed Mar. 29, 1982, now U.S. Pat. No. 4,487,199.

BACKGROUND OF THE INVENTION

1. Field of the Invention

This invention relates to a portable prosthetic device used to treat a human joint by applying "continuous passive motion".

2. Description of the Prior Art

Dr. Robert B. Salter, Professor and Head of Orthopaedic Surgery at the University of Toronto, and Senior Orthopaedic Surgeon at the Hospital for Sick Children in Toronto, first developed the concept and coined the expression "continuous passive motion". Dr. Salter's work is described in the article "Joints Were Meant to Move—And More Again" by Ohlendorf in "The Graduate", published by The Department of Information Services, University of Toronto, September/October 1980.

Briefly, according to this concept, a human joint, for example, a knee, elbow, or finger joint, is kept under slow continuous constrained motion as distinct from being held motionless or being moved intermittently. Keeping an injured or post operative joint mobile rather than immobilizing it in a cast is beneficial to the cartilage.

Attempts which have been made to provide machines that exercise joints are designed for intermittent operation and do not supply continuous passive motion. Moreover, they are usually too heavy and bulky to be readily portable and thus to be mounted on the body.

A primary aim of the present invention is to provide an apparatus which imparts continuous motion to the joint and which is portable so that it can be mounted on the patient's body.

SUMMARY OF THE INVENTION

An apparatus, according to the invention, includes a support structure, usually a housing containing working parts. Harness means mounts the support structure on the patient's body or, in an alternative arrangement, the support structure may be mounted on a crutch or bed. Traveller means is carried by the housing for reciprocating movement relative to it and is connected to an extremity of the limb having the joint to be exercised so that the joint completes the linkage. Motor means in the housing drives the traveller means back and forth through a predetermined stroke with a slow rhythmic motion.

BRIEF DESCRIPTION OF THE DRAWINGS

Having thus generally described the invention, it will be referred to more specifically by reference to the accompanying drawings, which illustrate preferred embodiments, and in which:

FIG. 6 is a fragmentary perspective showing an operating unit for treating the knee joint and which is connected to a bed on which the patient is reclining;

DESCRIPTION OF THE PREFERRED EMBODIMENTS

Figure 1:
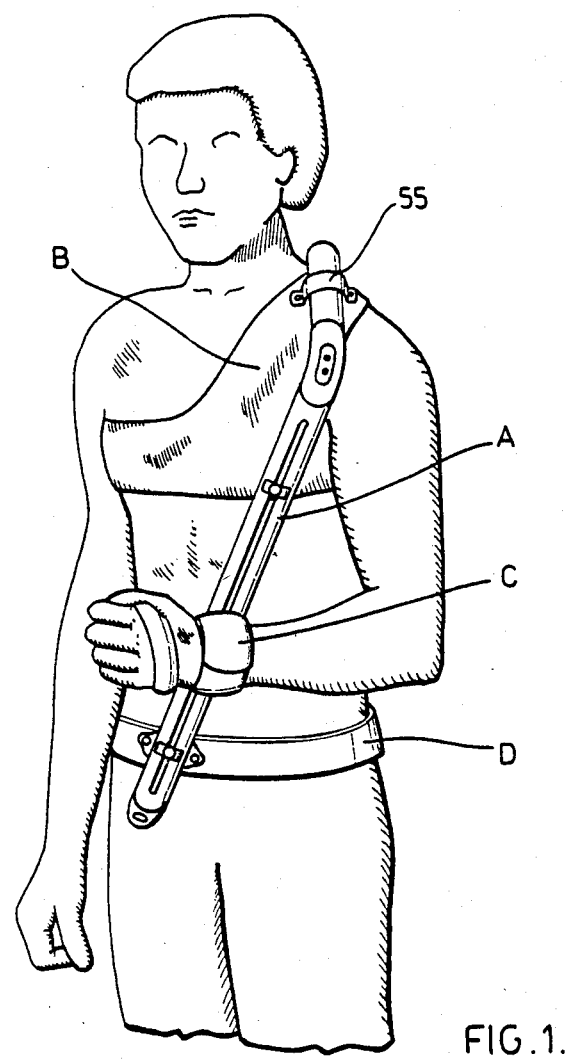
FIG. 1 is a perspective view showing a unit for treating an elbow joint.

Referring more particularly to FIG. 1, the device is made up of a support structure which, in this case, is an elongated housing A connected to the shoulder by a harness B and to the waist by a belt D. Actuator or traveller means, movable relative to the housing, is connected to the wrist by a cuff C. The traveller means is supported by the housing for linear reciprocating movement relative to it. Motor means drives the traveller means back and forth through a predetermined stroke in a slow rhythmic cycle. This imparts a corresponding reciprocating motion to the arm thus imparting continuous passive motion to the elbow joint.

The speed of movement of the actuator means would, in the embodiment shown, range from one-half foot to four feet per minute, or from one-third to two cycles per minute.

Figure 2:
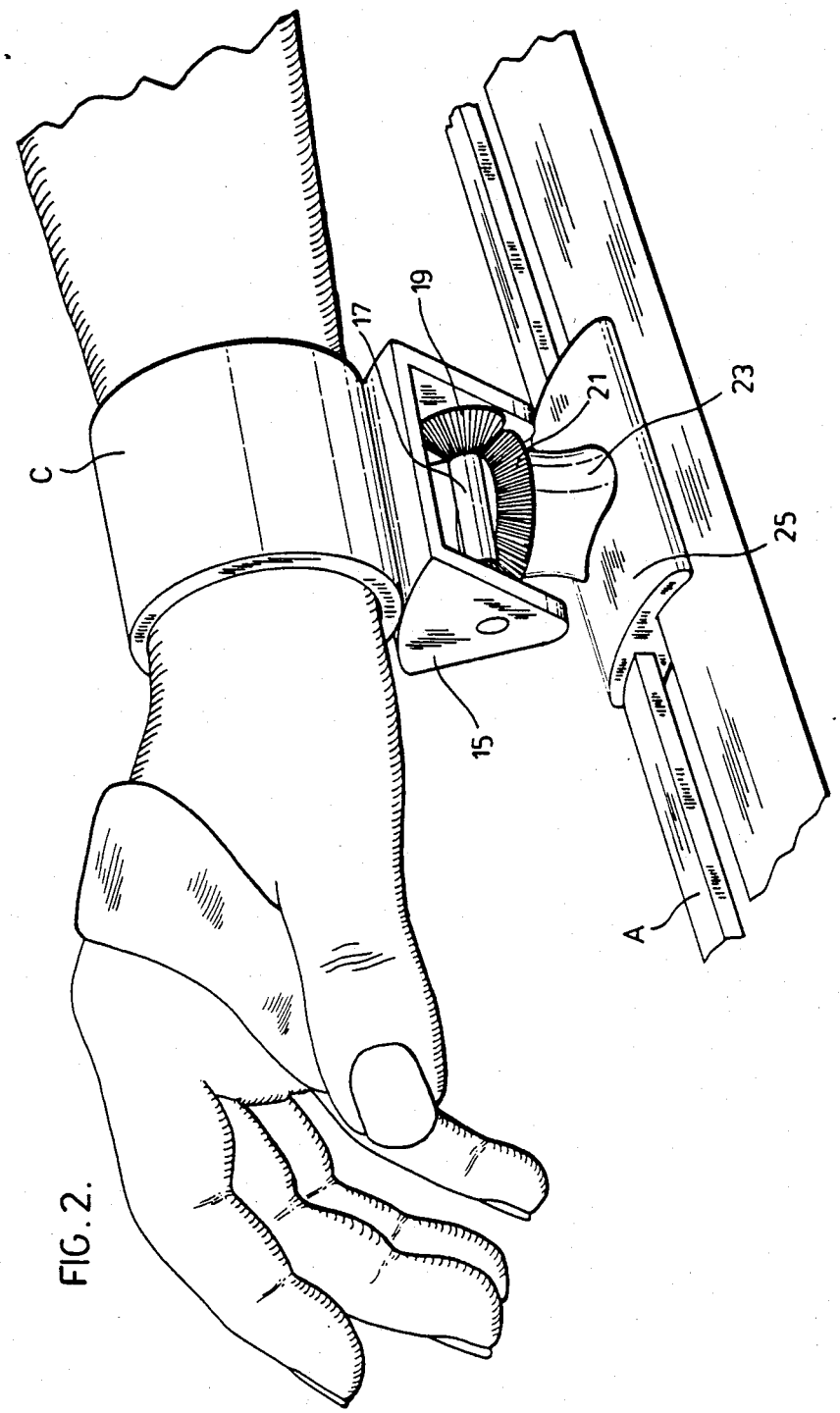
FIG. 2 is a greatly enlarged fragmentary perspective view showing the wrist connection in the unit of FIG. 1.

In order to supply supination and pronation to the wrist, the cuff C is connected (see FIG. 2) to a special mechanism. Mounted for rotation on a U-shape bracket 15 is a shaft 17, carrying a bevel gear 19, which meshes with a crown gear 21, carried on a hub 23, mounted on a plate 25 forming a part of the traveller means.

The plate 25 moves back and forth, along the housing A, and the flexing of the elbow causes rotation of the arm at the wrist, by virtue of its connection to the bevel gear 19 as it is caused to ride around the crown gear 21. At the same time, the wrist is held to the plate 25 so that it makes longitudinal movements with the latter along the housing A.

Figure 3:
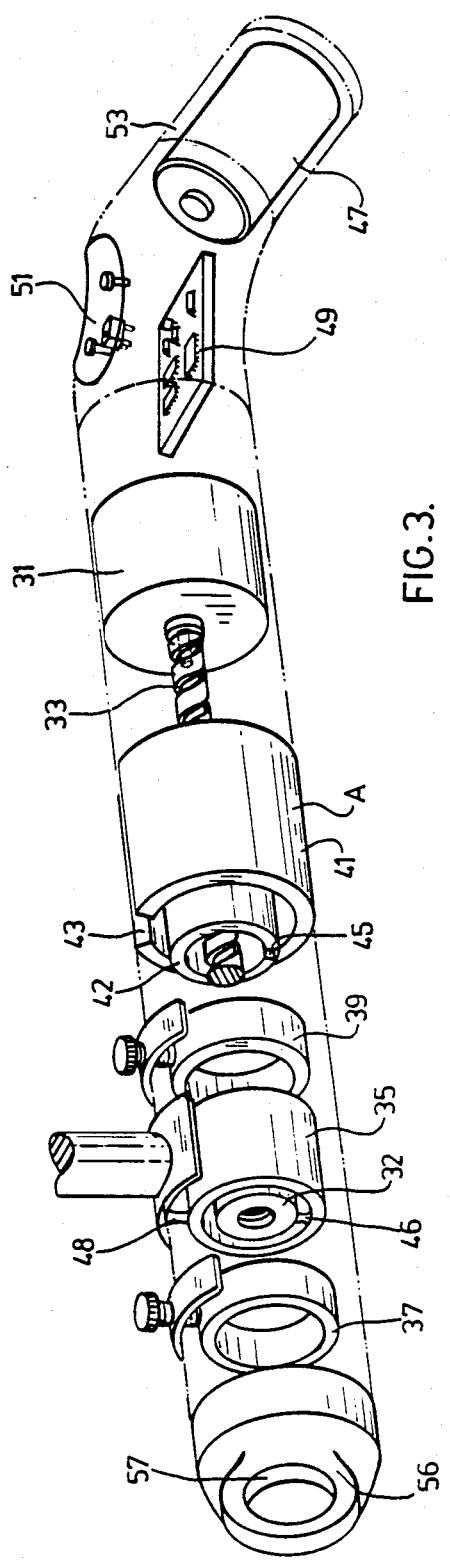
FIG. 3 is a schematic perspective diagram, of an exploded nature, showing the arrangement of the parts in a unit.

FIG. 3 shows in detail the support housing, actuating means, motor means and associated parts. A motor 31 drives an elongated screw 33 whose opposite end is rotatably held in a recirculating ball-type nut 32. A cylindrical slide 35 is connected to the nut 32 and moves linearly under the drive of the screw 33 between the limiting stops 37 and 39, which are locked to the housing A by thumb screws.

The mechanism is encased in an outer tube 41 and an inner concentric tube 42. The tube 41 is provided with a longitudinal slot 43 and the concentric tube 42 with an elongated slot 45. The slot 43 accommodates the flange connection 48 between the slide 35 and the plate 25. The slot 45 accommodates the flange connection 46 between the ball nut 33 and the slide 35.

The motor 31 is powered by batteries 47 which operate through circuits on a circuit board 49 and is governed by controls 51. The tube 41 is provided with a gooseneck part 53 about which there extends a bracket 55 connecting it to the harness B. The other end of the tube 41 has a terminal 56 provided with an eye 57 so that it can be hung from a suitable hook when required.

The motor 31 is a reversible motor. It will reverse as soon as an excessive load is applied. This may be, for example, where the actuator or traveller reaches the end of its stroke and is halted by the stop 37 or 39 as the case may be. Or, it may be where there is some unplanned obstruction, for example, sheets jamming in the mechanism or where the patient offers undue resistance. A safety function is thus performed as well as a prime actuating function.

Examples of suitable motors are geared D.C. Brush type motors made by Faulhaber, Escap, and Maxon Precision, all of Switzerland.

Figures 4, 5:
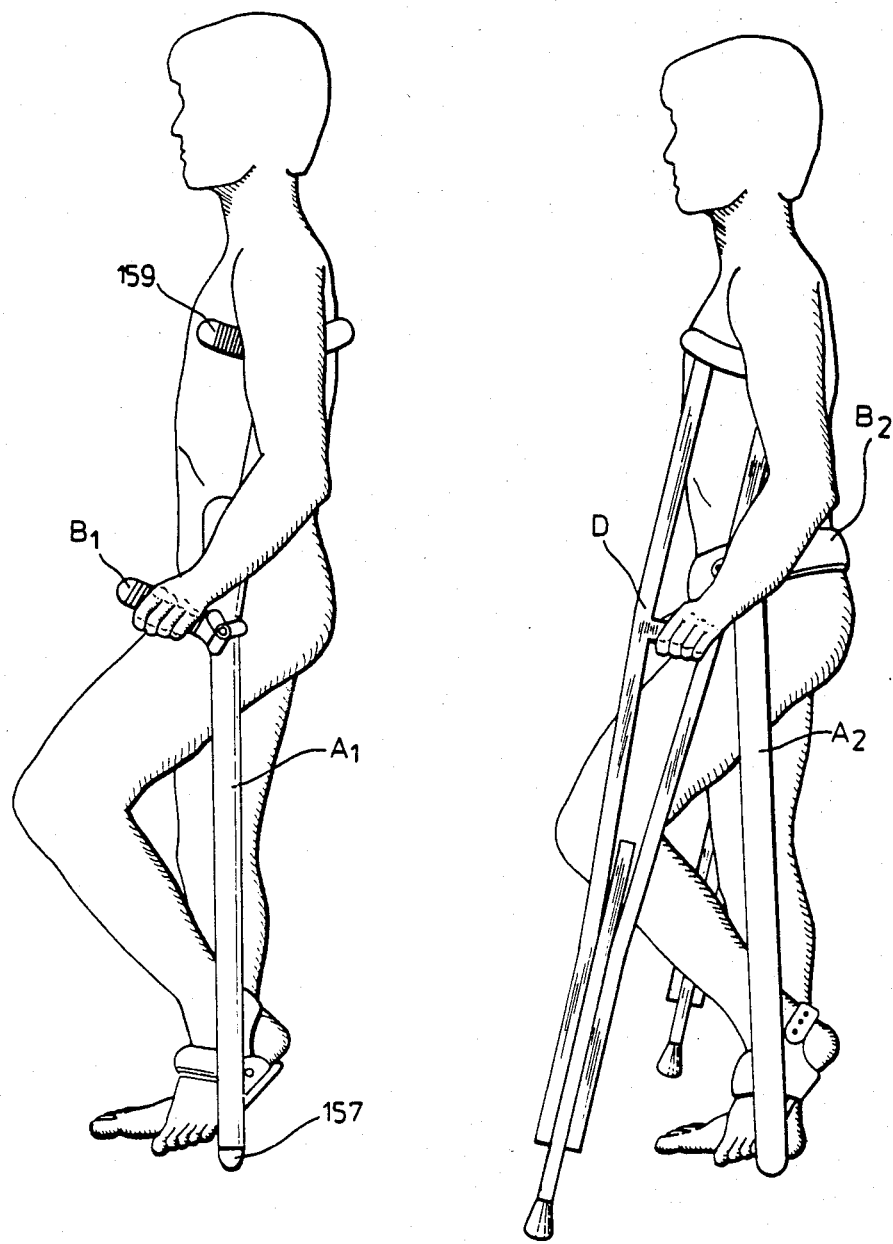
FIG. 4 is a side elevation showing a unit for treating the knee joint in which the unit forms part of a crutch.
FIG. 5 is a side elevation of a variation of the unit of FIG. 4.

FIG. 4 describes an apparatus for flexing the knee joint. Similar numbers have been applied to similar parts, as on FIGS. 1 and 3, with the exception that they have been raised by 100 and the letters have been given a subscript 1.

In this case, the support housing $A_1$ forms part of a crutch for supporting the patient and embodies operating mechanism similar to that shown in FIG. 3, except that the housing $A_1$ is straight instead of having a gooseneck end. It has a rubber foot 157 taking the place of the terminal 56. A handle $B_1$ takes the place of the harness B and is provided with an armpit bar 159. The part $B_1$ slides on the top end of the support housing $A_1$. Taking the place of the plate 25 is a simple foot plate with straps, as compared with the supination and pronation mechanism for rotating the wrist.

FIG. 5 shows an alternative arrangement in which a waistband $B_2$ is employed to connect the top of a support housing $A_2$ to the body. A separate crutch D supports the patient.

FIG. 6 illustrates a further form of leg exercising device. In this case, the support housing of FIGS. 4 and 5 is connected to a bed. It is retained by spaced-apart brackets 61 and 62. The leg of a patient lying on the bed is connected to the foot plate as in FIGS. 4 and 5.

Figure 7:
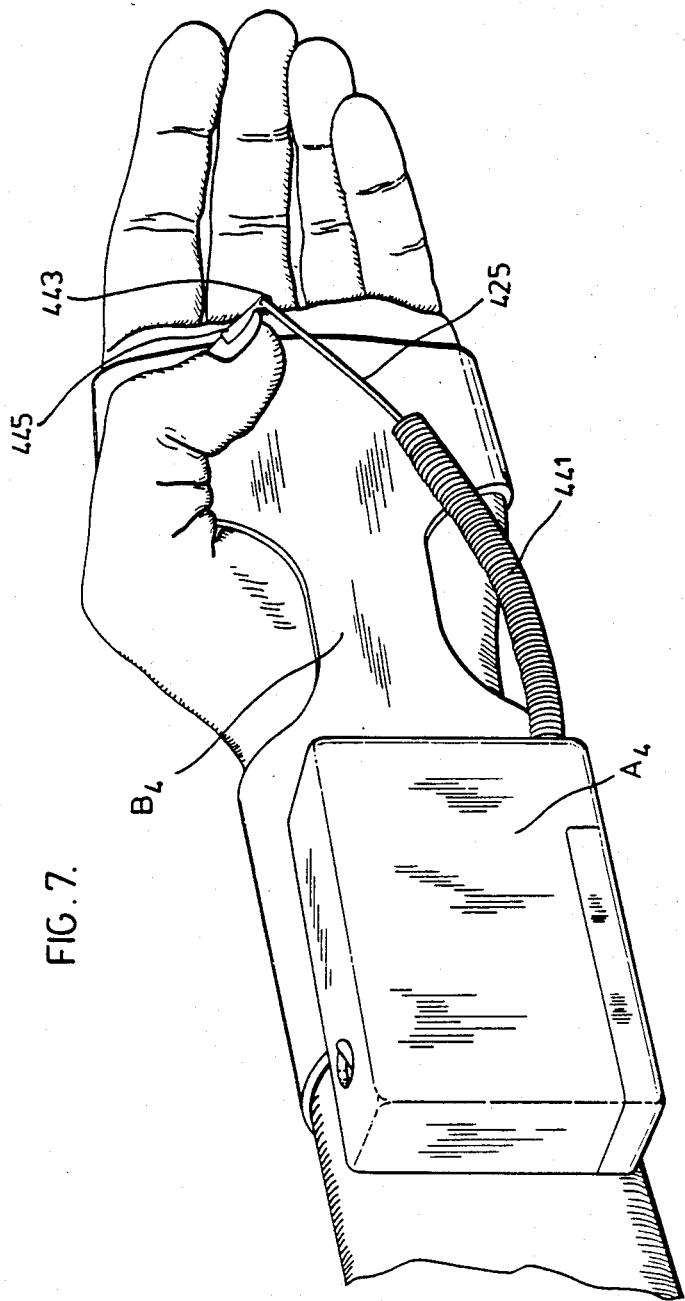
FIG. 7 is a fragmentary perspective view showing a unit for treating a finger or thumb joint.

FIG. 7 illustrates a device for flexing finger or thumb joints. Here again a support housing $A_4$ is connected to a cuff $B_4$ mounted on the wrist and hand in place of the harness of FIG. 1. An actuator wire 425 moves back and forth from the housing $A_4$, through a flexible guide tube 441, to a connection with the thumb.

The connection from the actuator wire 425 to the thumb is through a hinge 443 to a small plate 445, adhesively connected to the thumbnail. Alternatively, the actuator member 445 can be connected to any of the fingers or several fingers at a time.

Figure 8:
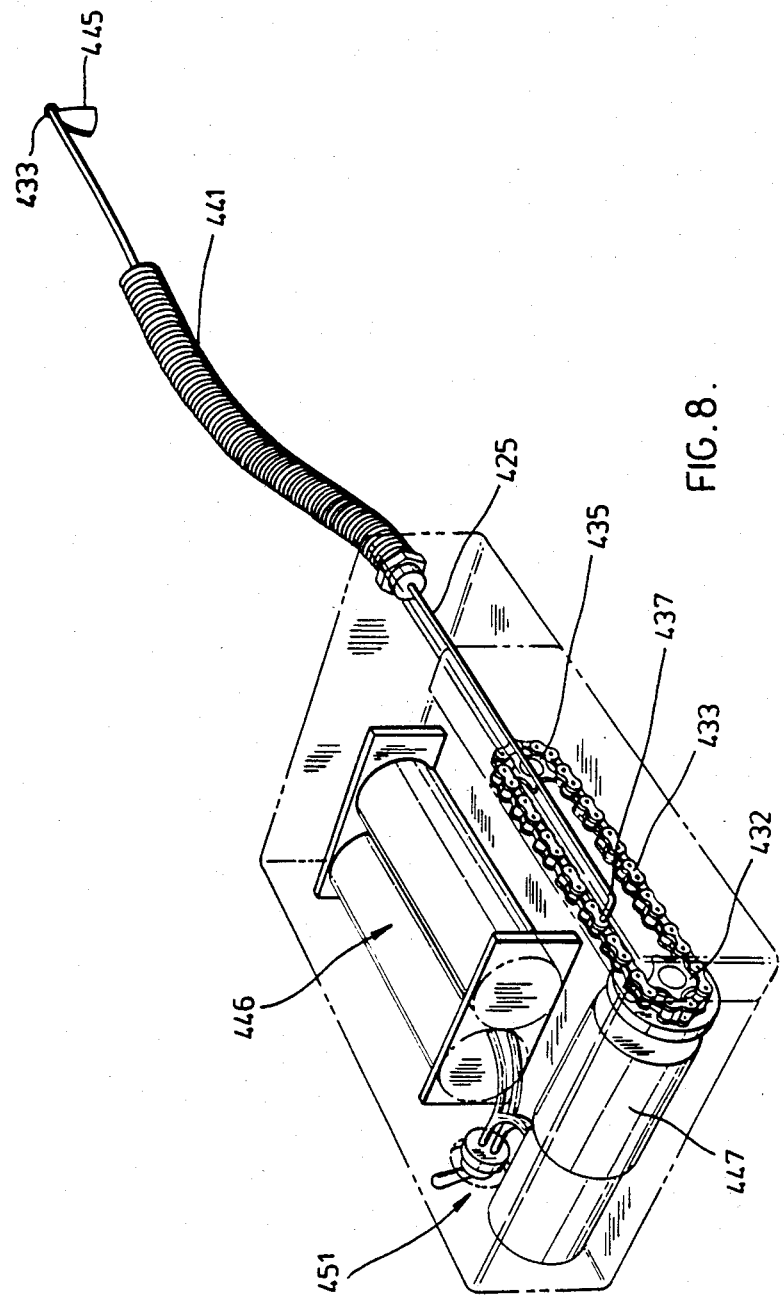
FIG. 8 is a perspective view of the unit shown in FIG. 7, illustrating the drive mechanism.

A mechanism for moving the actuator wire 425 is shown in FIG. 8. The support structure is fashioned from a block of plastic in which recesses have been made to accommodate the various parts. A geared motor 447 drives a sprocket 432 about which there is trained a chain 433 which is also trained about a spaced-apart sprocket 435. The actuator wire 425 is connected at 427 to one of the links of the chain 433. Batteries 446 are accommodated within the block as is an operating switch 451. The motor moves the chain continuously so that the actuator wire 425 moves in one direction along the top run of the chain and then down along the bottom run in the other direction so as to impart substantially continuous reciprocating movement to the wire 425 and consequently to the hand joint.

From this detailed description it will be evident that various modifications can be made within the spirit of the invention to treat various joints of the body under appropriate conditions.

I claim:

1. An actuator for imparting back and forth motion in a slow rhythmic cycle, comprising,
   a support housing having a longitudinal slot defining a guide track,
   a traveller operatively mounted to said support housing for back and forth motion relative to said housing,
   a tubular housing mounted in said support housing, said tubular housing having a longitudinally extending slot offset relative to said guide track, and
   a drive member mounted inside said tubular housing adapted to drive said traveller with said back and forth motion, said traveller including a travel element mounted inside said support housing operatively connected through the longitudinally extending slot in said tubular housing to said drive member, said travel element being connected to a travel member mounted for travel along said guide track.

2. An actuator according to claim 1, further including motor means to drive member, said motor means being housed inside said housing.

3. An actuator according to claim 1, wherein said tubular housing is centrally disposed in said support housing and said drive member is centrally disposed in said tubular housing.

4. An actuator according to claim 1, wherein said drive member comprises a drive screw having a screw thread mounted for rotation inside said tubular housing, and said travel element is mounted on said drive screw for movement relative to said thread, said travel element being restrained against rotary movement with said drive screw such that rotary movement of said drive screw is converted into longitudinal movement of said travel element whereby said travel member moves along said guide track.

5. An actuator according to claim 4, wherein said travel element comprises nut means mounted on said drive screw.

6. An actuator according to claim 4, wherein said travel element comprises an inner nut member mounted on said drive screw, inside said tubular housing, and an outer member held to said nut member by connecting means extending through said longitudinal slot in said tubular housing, said outer member being mounted to travel between said support housing and said tubular housing, and including a pair of spaced-apart terminal stops in said support housing to define said predetermined stroke.

7. An actuator according to claim 6, further including motor means to drive said drive screw, said motor being reversible, whereby it drives the traveller first in one direction and then in the other to cause reciprocating movement of the traveller.

8. An actuator according to claim 7, including means to reverse the direction of the motor within said predetermined stroke, when a predetermined excessive load is applied to said motor means during said travel stroke.

9. An actuator according to claim 8, wherein said means to reverse the direction is actuatable by predetermined resistance of the screw member to rotation.

10. An actuator according to claim 9, wherein said motor means is housed inside said support housing.

11. An actuator according to claim 4, wherein said tubular housing is centrally disposed in said support housing and said drive screw is centrally disposed in said tubular housing.

12. An actuator according to claim 1, further including means for reversing the direction or travel of said traveller, when a predetermined load is applied to said traveller, during said back and forth motion.

* * * * *